United States Patent
Belz et al.

(10) Patent No.: US 11,128,709 B2
(45) Date of Patent: Sep. 21, 2021

(54) METHOD AND APPARATUS FOR RECEIVING NUTRITIONAL INFORMATION VIA A NETWORK

(71) Applicants: AT&T Intellectual Property I, L.P., Atlanta, GA (US); AT&T Mobility II LLC, Atlanta, GA (US)

(72) Inventors: Steven Belz, Sunnyvale, TX (US); Greg W. Edwards, Austin, TX (US); Michael Lattanzi, Bothell, WA (US); Constance Missimer, Seattle, WA (US); James H. Pratt, Round Rock, TX (US)

(73) Assignees: AT&T INTELLECTUAL PROPERTY I, L.P., Atlanta, GA (US); AT&T MOBILITY II LLC, Atlanta, GA (US)

( * ) Notice: Subject to any disclaimer, the term of this patent is extended or adjusted under 35 U.S.C. 154(b) by 1252 days.

(21) Appl. No.: 14/970,495

(22) Filed: Dec. 15, 2015

(65) Prior Publication Data
US 2017/0169189 A1    Jun. 15, 2017

(51) Int. Cl.
*H04L 29/08* (2006.01)
*G16H 20/60* (2018.01)

(52) U.S. Cl.
CPC ............. *H04L 67/12* (2013.01); *G16H 20/60* (2018.01); *H04L 67/306* (2013.01)

(58) Field of Classification Search
CPC .... G06F 19/3475; H04L 67/306; H04L 67/12
See application file for complete search history.

(56) References Cited

U.S. PATENT DOCUMENTS

| 6,283,914 B1 | 9/2001 | Mansfield et al. |
| 6,580,360 B1 | 6/2003 | McKee et al. |

(Continued)

FOREIGN PATENT DOCUMENTS

| DE | 29917576 U1 | 10/1999 |
| EP | 2246814 | 11/2010 |

(Continued)

OTHER PUBLICATIONS

Gao, Chunming, Fanyu Kong, and Jindong Tan. "Healthaware: Tackling obesity with health aware smart phone systems." Robotics and Biomimetics (ROBIO), 2009 IEEE International Conference on. Ieee, 2009. https://www.researchgate.net/profile/Chunming_Gao/publication/224118484_HealthAware_Tackling_obesity_with_health_aware_smart_phone_systems/links/00b4953c5ae67249ff000000.pdf Discloses "The system presents the user's physical activity counts at real time to remind how much daily activity is needed to keep healthy. The user takes pictures of food items and the system provides health related information regarding to the food item intakes. The system is composed of an ondevice database which holds the user specific data and food item information."

(Continued)

*Primary Examiner* — Linh Giang Le

(57) ABSTRACT

A method and apparatus for receiving nutritional information are disclosed. For example, the method receives a profile of a user, receives over the communications network, grocery information on one or more grocery items at one or more locations of the user, receives over the communications network, ingestion information on ingestion by the user of at least one grocery item from the one or more grocery items, generates nutritional information, wherein the nutritional information is determined by performing an analysis based on the profile of the user, the grocery information, and the ingestion information, and provides over the (Continued)

communications network, the nutritional information, to an endpoint device of the user.

20 Claims, 4 Drawing Sheets

(56) References Cited

U.S. PATENT DOCUMENTS

| | | | |
|---|---|---|---|
| 6,735,479 | B2 | 5/2004 | Fabian et al. |
| 6,758,397 | B2 | 7/2004 | Caton |
| 6,892,545 | B2 | 5/2005 | Ishikawa et al. |
| 7,493,362 | B2 | 2/2009 | Bogatin et al. |
| 8,092,345 | B2 | 1/2012 | Ellis et al. |
| 8,601,005 | B2 | 12/2013 | Bousamra et al. |
| 8,684,922 | B2 | 4/2014 | Tran |
| 8,770,983 | B2 | 7/2014 | Batsikouras |
| 2002/0016734 | A1 | 2/2002 | McGill et al. |
| 2003/0065575 | A1 | 4/2003 | Berkema |
| 2005/0049920 | A1* | 3/2005 | Day ............... G06Q 30/06 705/15 |
| 2008/0034001 | A1 | 2/2008 | Noel |
| 2009/0239440 | A1 | 9/2009 | Kang |
| 2012/0183932 | A1 | 7/2012 | Chang et al. |
| 2013/0052946 | A1 | 2/2013 | Chatterjee et al. |
| 2014/0095479 | A1 | 4/2014 | Chang et al. |
| 2014/0122280 | A1 | 5/2014 | Jung et al. |
| 2014/0165614 | A1* | 6/2014 | Manning ............ F25D 29/00 62/62 |
| 2015/0118659 | A1 | 4/2015 | Meyer |
| 2015/0132725 | A1 | 5/2015 | Okubo et al. |
| 2016/0179065 | A1* | 6/2016 | Shahabdeen ........ G05B 15/02 700/275 |
| 2016/0180723 | A1* | 6/2016 | Tatourian ............ G09B 5/00 434/237 |

FOREIGN PATENT DOCUMENTS

| | | | |
|---|---|---|---|
| JP | 2000310476 | | 11/2000 |
| JP | 2001041628 | | 2/2001 |
| JP | 2004164038 A | * | 6/2004 |
| WO | WO 2014/016212 | | 1/2014 |

OTHER PUBLICATIONS

Reddy, Sasank, et al. "Image browsing, processing, and clustering for participatory sensing: lessons from a DietSense prototype." Proceedings of the 4th workshop on Embedded networked sensors. ACM, 2007. http://citeseerx.ist.psu.edu/viewdoc/download?doi=10.1.1.124.5729&rep=rep1&type=pdf Discloses "ImageScape was designed as an analysis component of DietSense, a software system under development at UCLA to support (1) the use of mobile devices for automatic multimedia documentation of dietary choices with just-in-time annotation, (2) efficient post facto review of captured media by participants and researchers, and (3) easy authoring and dissemination of the automatic data collection protocols."

Krishnamurthy, Gaurav. "NutriSurface, A Smart Nutritional Scale That Promotes Healthy Eating (Interview)." medGadget, medgadget.com, Oct. 10, 2013. http://www.medgadget.com/2013/10/nutrisurface-a-smart-nutritional-scale-that-promotes-healthy-eating-interview.html Discloses weight measuring devices for purposes of nutrition monitoring.

McGrath, Jenny. "SmartPlate uses cameras and sensors to determine your dinner's nutritional value." Digital Trends, digitaltrends.com, May 4, 2015. http://www.digitaltrends.com/home/smartplate-knows-the-nutrition-info-of-your-meals/ Discloses plate relating nutritional information of meal throughout weight and nutritional database.

Wiggers, Kyle. "How many calories are in that sundae? Google will tell you with the snap of a picture." Digital Trends, digitaltrends.com, Jun. 3, 2015. http://www.digitaltrends.com/photography/google-calorie-counter-news/ Discloses smart phone taking pictures of food and receiving nutritional information via a database.

* cited by examiner

METHOD AND APPARATUS FOR RECEIVING NUTRITIONAL INFORMATION VIA A NETWORK

The present disclosure relates to a method and apparatus for receiving nutritional information via a communications network, e.g., a communications network of a network service provider.

BRIEF DESCRIPTION OF THE DRAWINGS

The teaching of the present disclosure can be readily understood by considering the following detailed description in conjunction with the accompanying drawings, in which.

To facilitate understanding, identical reference numerals have been used, where possible, to designate identical elements that are common to the figures.

DETAILED DESCRIPTION

Figure 1:
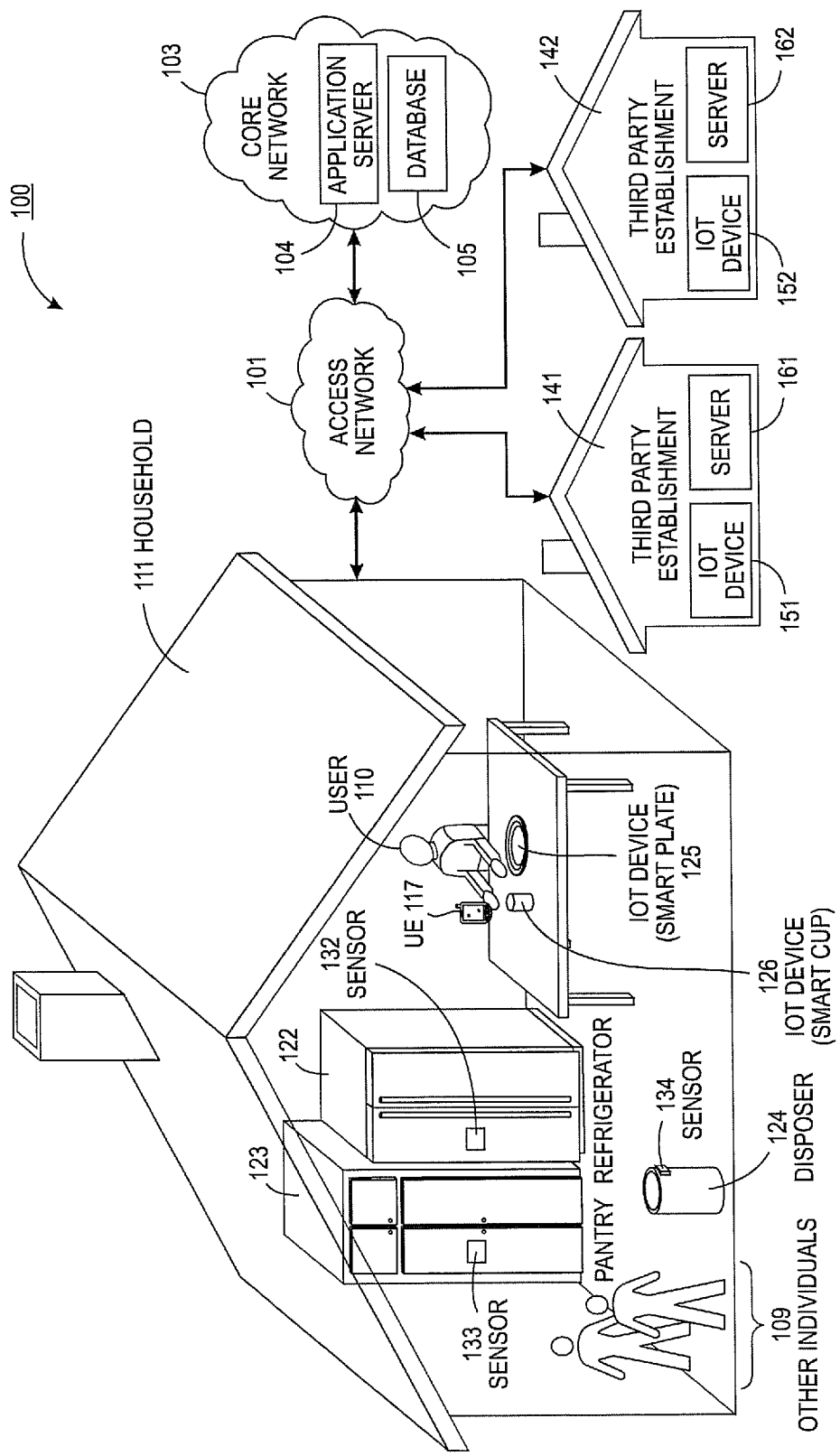
FIG. 1 illustrates an example network related to the present disclosure.

The present disclosure relates to a method and apparatus for receiving nutritional information via a communications network, e.g., a communications network of a communications network service provider (broadly a network service provider). The teachings of the present disclosure can be applied via any type of wired or wireless communications network.

A user may wish to improve the nutritional value of food and drink items that are consumed. For example, the user may be health conscious and may wish to maintain or improve his/her health. One approach may involve keeping track of food and drink consumption, tabulating the date, and then making an assessment as to whether or not the consumption was consistent with good nutrition. However, this manual approach requires that the user actively records such information every time an instance of food item or drink is consumed. The approach is labor intensive and it is likely that the user may abandon this effort once it becomes too burdensome. In addition, when a desired goal is not reached, the cause for the failure may not be known. For example, the user may not have the necessary knowledge of what he/she should eat to maximize his/her health. The user may then benefit from receiving nutritional information that is based on a profile of the user, and an automated recording of ingestions of food and/or drink items by the user.

In one embodiment, the present disclosure describes a method for receiving nutritional information that is based on the profile of the user, and an automated recording of ingestions of food and drink items by the user. For example, a user may receive nutritional information from a server of a network service provider via a user endpoint device, e.g., a smart phone.

In order to clearly illustrate the teachings of the current disclosure, the following terminologies will first be described:

Internet of Things; and
Sensor.

Internet of Things (IoT) refers to a network of objects, e.g., devices having the necessary electronics, software, and network connectivity to collect and exchange data. For example, the Internet of Things devices may have Internet Protocol addresses for Internet connectivity. An object that is part of the IoT network may be referred to as an IoT object or IoT device. An IoT device has the ability to send and/or receive data without requiring a human-to-human or a human-to-computer interaction.

A sensor refers to a device that detects an event or a change and provides an output that indicates the event or the change that is detected. Said another way, the sensor may also refer to a device that is tasked with measuring a physical quantity. The sensor may be an IoT device.

In one embodiment of the present disclosure, the present method provides a network-based nutritional tracking service provided by a network service provider. For an illustrative example, a user A may wish to receive nutritional information (e.g., comparative nutritional information of User A as compared to the general population, comparative nutritional intake of User A as compared to a "model" individual of comparable age and gender, and so on) from a network service provider that is based on the profile of user A, and a record of food and/or drink items ingested by the user A. For example, the network service provider may obtain the profile of the user A which may include the age, gender, weight, and various biometric information (e.g., blood pressure, glucose level, body temperature, etc.) of user A. Such profile can be provided directly by the user A or is provided by a source authorized by user A, e.g., a social networking site hosting such a profile for user A.

However, since user A may ingest food and drink items throughout the day from various locations, the network service provider may need to determine a list of grocery items (e.g., broadly grocery information comprising a list of available food and/or drink items) in one or more locations at which user A may have consumed these grocery items. In one example, the service provider may need to obtain a list of food and drink items in a household of user A. In another example, the service provider may need to obtain a list of food and drink items in other locations, e.g., a restaurant, a work environment, an educational institution and so on, at which the user A may have ingested these food and drink items. Having the list of available food and/or drink items will assist in accurately determining what items from the list of available food and/or drink items that user A may have actually ingested throughout the day. Said another way, in one example the accurate recordation of the actual food and/or drink items consumed by user A will need to be determined. Knowing what food and/or drink items are available at any particular location as a starting point may serve as a confirmation as to the actual food and/or drink items that the system may have detected having been ingested user A. For example, if the list of grocery items includes milk, orange juice, and apple juice, and the user A is detected as having ingested milk in the morning, then the confidence level for such detection will be deemed to be high. Alternatively, if the user A is detected as having ingested coffee in the morning or an alcoholic beverage at night, then the confidence level for such detection will be deemed to be low if such detected items were not initially detected as part of the grocery items. It should be noted that having a low confidence level does not, in and of itself, indicates that the detected ingestion of the particular item by user A is incorrect (e.g., the coffee is a formulated item that is assembled from a plurality of different ingredients, the coffee or alcoholic beverage could have been brought by a guest visiting user A, and so on).

In one embodiment, the food and/or drink items actually ingested by user A is determined and recorded. The manner in which food and/or drink items being detected as ingested by user A will be further described below. The information on the ingestion of these food and drink items may be recorded over a period of time by the network service provider. The recorded information may be stored in a server or uploaded to a cloud storage. The network service provider may then perform an analysis that is based on the ingestion information and the profile of user A. The service provider may then provide the nutritional information to user A based on the result of the analysis. For example, the service provider may gather the various types of information described above for user A, compare user A's information to a population based nutritional information, and provide nutritional information for user A based on the profile of user A as compared to the general population. For instance, when compared with people who are of a same age, gender and weight of the user A, the analysis may indicate that User A needs to consume more or less of certain food and/or drink items, e.g., an additional glass of milk during breakfast time.

Alternatively, the comparison can be made against a "model individual" (or broadly a nutritional model) of a same age, gender and weight of the user A, that is selected by user A. In other words, nutritional science is an evolving field where there are many different opinions as to what may constitute a proper or healthy diet. Said another way, there may be several different food-based dietary guidelines that are promoted by different organizations. Thus, the network service provider will accord user A an option to select one of those food-based dietary guidelines that user A prefers to follow. Thus, user A may dynamically select one nutritional model from a plurality of different nutritional models that is made available by the network service provider.

FIG. 1 illustrates an example network 100 related to the present disclosure. In one illustrative embodiment, the network 100 comprises a household 111, an access network 101, a core network 103, and various third party establishments 141-142.

For example, the household 111 may comprise a user 110 and other individuals 109. The user 110 may access various network services, e.g., telephony services, data services, Internet access services, multi-media delivery services and the like, via a user endpoint (UE) device 117, e.g., a cell phone, a smart phone or a computing tablet. The household 111 may also comprise a plurality of IoT devices 122-126. The third party establishments 141-142 may also comprise a plurality of IoT devices 151-152 and servers 161-162, respectively. The IoT devices 122-126 and 151-152 may access services, e.g., Internet services, from the core network 103 via the access network 101.

In one embodiment, the access network 101 may comprise a Wireless-Fidelity (Wi-Fi) network, a cellular network (e.g., 2G, 3G, and the like), a long term evolution (LTE) network, and the like. The core network 103 may comprise any type of communications network, such as for example, a traditional circuit switched network (e.g., a public switched telephone network (PSTN)) or a packet network such as an Internet Protocol (IP) network (e.g., an IP Multimedia Subsystem (IMS) network), an asynchronous transfer mode (ATM) network, or a wireless network. It should be noted that an IP network is broadly defined as a network that uses Internet Protocol to exchange data packets.

Figure 4:
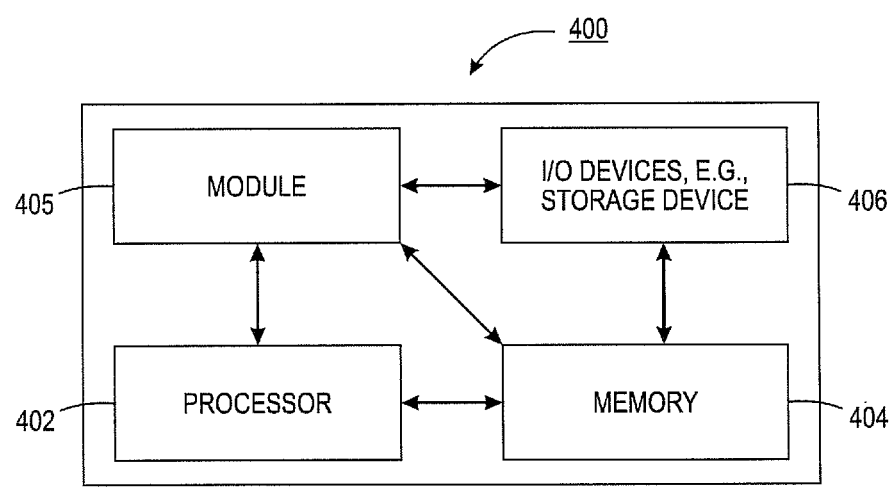
FIG. 4 depicts a high-level block diagram of a computer suitable for use in performing the functions described herein.

In one embodiment, the UE 117 may be deployed as a hardware device embodied as a dedicated device (e.g., the dedicated computer 400 as illustrated in FIG. 4). In one embodiment, the UE 117 is configured to perform the methods and functions described herein (e.g., the method 200 discussed below). For example, the UE 117 of the present disclosure is for obtaining a profile of the user to be forwarded to a network service provider, determining a list of grocery items (e.g., a listing of available food and/or drink items) in one or more locations at which the user may consume such grocery items, obtaining ingestion information on the actual ingestion of particular food and/or drink items by the user (e.g., particular food and/or drink items from the list of grocery items), storing the gathered information (e.g., a listing of grocery items, particular food and/or drink items from the list of grocery items that are detected to have been ingested, the locations where these particular food and/or drink items are ingested and the like), providing the information that is gathered to a network service provider for analysis, and receiving nutritional information from the network service provider. The nutritional information that is received is based on an analysis of the ingestion information and the profile provided to the network service provider. In one embodiment, the nutritional information that is received is further based on a comparison of the ingestion information and the profile of the user to those of a population in a geographical area, or to a nutritional model.

In one embodiment, the core network 103 may include an application server (AS) 104, and a database (DB) 105. For example, the AS 104 may be deployed as a hardware device embodied as a dedicated database server (e.g., the dedicated computer 400 as illustrated in FIG. 4). In one embodiment, the AS 104 is configured to perform the methods and functions described herein (e.g., the method 300 discussed below). For example, the network service provider provides a subscribed service to a user where the user is able to receive nutritional information. For example, the user may receive nutritional information based on an analysis of the user's profile and ingestion information e.g., a record of ingestion of food and/or drink items. In turn, the user may then utilize the nutritional information received from the network service provider to make better decisions as to what food and/or drink items to ingest. In other words, a user may want to improve his/her health and subscribe to a service to receive nutritional information for improving the nutritional value of food/drink items that the user may procure.

In one embodiment, the database 105 is used for storing various data, e.g., profiles of users, locations of sensors, capabilities of sensors, data gathered via sensors, etc. For example, the profile of a user may include one or more of: an identity of the user, information for identifying the user (a voiceprint of the user, a fingerprint scan of the user, a retina scan of the user, etc.), one or more biometric measurements of the user (e.g., blood pressure, glucose level, temperature readings, etc.), an age of the user, a gender of the user, a weight of the user, a height of the user, a race of the user, and the like.

In one embodiment, the AS 104 is used for providing nutritional information to a user. For example, the AS 104 of the present disclosure is for obtaining or receiving the profile of the user, determining a list of grocery items in one or more locations at which the user may consume certain items from the list of grocery items, obtaining ingestion information on particular food and drink items from the list of grocery items ingested by the user, analyzing the ingestion information and the profile by comparing to a "population based nutritional information," or a "model based nutritional information," and providing the nutritional information to the user. The user may then utilize the nutritional information that is received from the network service provider as a guide for making food and/or drink consumption decisions or procurement decisions.

It should be noted that the network 100 may include additional networks and/or elements that are not shown to simplify FIG. 1. For example, the access network and the core network of FIG. 1 may include additional network elements (not shown), such as for example, base stations, border elements, gateways, firewalls, routers, switches, call control elements, various application servers, and the like.

Although a single database is shown in FIG. 1, the various types of data may be stored in any number of databases. For instance, various databases, e.g., a separate database for profiles of users, a separate database for data gathered from various sensors, etc., may be used. In addition, the various types of data may be stored in a cloud storage. In other words, the network service provider may implement the service for providing nutritional information of the present disclosure by utilizing distributed IoT devices (e.g., distributed sensors), and user profiles that are established and stored in a cloud storage and/or a centralized server.

In one embodiment, the user 110 may consume food and drink items via IoT devices 125-126. For example, the IoT device 125 may comprise a food serving dish (e.g., a plate or a bowl) with one or more sensors, e.g., a smart dish, and the IoT device 126 may comprise a drinking container (e.g., a cup, a glass, a mug or a tumbler) e.g., a smart container. For simplicity, the IoT devices 125 and 126 may be referred to as a smart dish and a smart container, respectively.

In one embodiment, the smart dish 125 comprises one or more sensors for determining one or more of: a type of food item placed on the smart dish (e.g., an optical sensor or a camera for capturing an image of the food item on the dish), a quantity of a food item placed on the smart dish (e.g., a weight sensor or a pressure sensor), an identity of a person ingesting a food item via the smart dish (e.g., a fingerprint scanner or a code scanner or receiver receiving a signal, e.g., from a wrist band wore by a user handling or is proximate to the smart dish consistently for a prolong period of time, e.g., 15-30 minutes for eating a meal), a quantity of a food item remaining on the smart dish when the person stops ingesting the food item, etc. In one embodiment, the smart container comprises a sensor for determining one or more of: a type of drink item placed into the smart container (e.g., an optical sensor or a camera for capturing an image of the drink item poured into the container, a scanner detecting a signal from the container from which the drink is poured from, e.g., a RF tag embedded into a milk or juice container), a quantity of a drink item placed on the smart container (e.g., a weight sensor, a volume sensor, or a pressure sensor), an identity of a person ingesting a drink item via the smart container (e.g., a fingerprint scanner or a code scanner or receiver receiving a signal, e.g., from a wrist band wore by a user handling or is proximate to the smart container consistently for a prolong period of time, e.g., 2-15 minutes for drinking a beverage), a quantity of a drink item remaining in the smart container when the person stops ingesting the drink item, etc.

In one embodiment, the smart dish or smart container may contain any number of different food and/or drink items. Thus, the smart dish or smart container may identify each type of food or drink item that is being ingested, the quantity of each type of food or drink item that is being ingested, the identity of the person ingesting the food or drink item, and the leftover quantities for each type of food or drink item.

In one embodiment, the IoT devices 122-124 may comprise appliances, storage units or spaces for storing grocery items. For example, the IoT device 122 may be a smart refrigerator (or freezer, or combination thereof), the IoT device 123 may comprise a smart pantry, the IoT device 124 may comprise a smart disposer 124, e.g., a trash container, etc. The IoT devices 122-124 may comprise one or more sensors 132-134, respectively, for determining when a grocery item is deposited in or removed from a respective IoT device 122, 123 or 124, e.g., time stamps can be generated and stored as items are deposited or removed. In addition, the sensor 132, 133 or 134 may determine the identity of the person depositing or removing the grocery item (e.g., the person may be wearing a wrist band having an identifier, e.g., an RF ID tag or a transmitter emitting an ID signal representing the wearer of the wrist band).

For example, the smart refrigerator 122 may comprise the sensor 132 for determining information for a grocery item that is contained within the smart refrigerator. The information for the grocery item may comprise one or more of: the type of the grocery item, the time that the grocery item is deposited into the refrigerator, the time that the grocery item is removed from the refrigerator, an identity of the person depositing or removing the grocery item, a quantity of the grocery item being deposited or removed, a quantity of the grocery item remaining in the refrigerator, a duration of time that the grocery item is stored inside the smart refrigerator, a duration of time that the grocery item is removed from the smart refrigerator before it is returned (or it is never returned if the grocery item is completely consumed or has been discarded) and so on.

In another example, the smart pantry 123 may comprise the sensor 133 for determining information for a grocery item that is contained within the smart pantry. Similarly, the information for each grocery item as captured by sensor 133 may comprise one or more of: the type of the grocery item, the time that the grocery item is deposited into the smart pantry, the time that the grocery item is removed from the smart pantry, an identity of the person depositing or removing the grocery item, a quantity of the grocery item being deposited or removed, a quantity of the grocery item remaining in the smart pantry, a duration of time that the grocery item is stored inside the smart pantry, a duration of time that the grocery item is removed from the smart pantry before it is returned (or it is never returned if the grocery item is completely consumed or has been discarded) and so on.

In another example, the smart disposer 124 may comprise the sensor 134 for determining information for a grocery item that is disposed into the smart disposer. Similarly, the information for each grocery item as captured by sensor 134 may comprise one or more of: the type of the grocery item, the time that the grocery item is deposited into the smart disposer, an identity of the person depositing the grocery item, a quantity of the grocery item being deposited, and so on.

It should be noted that each of the sensors 132-134 may in fact comprise a plurality of sensors. The illustration of a single sensor for the refrigerator, pantry and disposer in FIG. 1 is for clarity reason only. In one embodiment, the sensors 132-134 may comprise a scanner or a radio receiver, e.g., a fingerprint scanner, a retina scanner, a voiceprint scanner, an RF receiver, etc., for identifying the person depositing or removing the food/drink item. For example, a fingerprint, a retina print, a voiceprint and/or an RF code can be captured or assigned for each user, e.g., capturing a fingerprint of each individual within a household, or assigning a code to a wrist band to be wore by each individual within the house hold. In one embodiment, the sensors 132-134 may further comprise various types of code scanners, e.g., bar code scanners, QR code scanners, and/or RF tag scanners, to obtain information pertaining to various grocery items, e.g., detecting a bar code on a milk container, a juice container, a bag of coffee, a bag of apples, a can of soup, and the like. In one embodiment, the sensors 132-134 may further comprise various types of optical sensors, e.g., a photodiode, an array of photodiodes, a camera and the like) for detecting various waves of various wavelengths. For example, an image can be captured of the packaging of a grocery item, of an individual, of a location, and so on. The captured image can be used to identify the type of a grocery item or an individual, e.g., comparing the captured image to a stored image. In one embodiment, the sensors 132-134 may further comprise various types of contact or motion sensors for detecting various motions or opening/closing of access doors or panels. For example, a contact sensor located on a door may trigger a scanner or a camera to capture an RF tag code or to take a picture when the door is opened or closed, e.g., a refrigerator door, a pantry door, a disposer door, and so on. In one embodiment, the sensors 132-134 may further comprise various types of communications interface and components, e.g., receivers, transmitters, transceivers, to communicate with a cellular tower, a local router, a local gateway, and so on. For example, a contact sensor located on a door may trigger a scanner or a camera to capture an RF tag code or to take a picture when the door is opened or closed. In turn, the gathered data, e.g., the scanned code and/or the captured image can then be transmitted via the transceiver to an application server operated by a network service provider.

Thus, any combinations of different types of sensors can be deployed to identify a grocery item and/or an individual. It should be noted that the term "smart" is only used herein as a relative term, e.g., an electronic device, generally connected to other devices or networks via various types of wireless communication protocols, e.g., cellular communication, wireless fidelity communication, personal network communication, e.g., Bluetooth, and the like. As such, a smart refrigerator is "smart" in the sense that data can be captured and communicated to other devices for a particular environment. As such, it should not be interpreted solely that the refrigerator must be originally manufactured with the necessary electronic components to make the refrigerator a smart refrigerator. For example, one alternate embodiment is to simply deploy the various sensors 132, 133, and 134 as a package of sensors that can be deployed within a confined environment, e.g., deploying the sensor 132, into a cabinet or a storage area of a home. Said another way, although the "smart" pantry or "smart" refrigerator can be manufactured as a consolidated unit, e.g., a cabinet preinstalled with the various sensors or a refrigerator preinstalled with the various sensors, the pantry or refrigerator may simply be a closet or a traditional refrigerator located in a kitchen area of a home, with various sensors that are subsequently added into the closet or refrigerator.

The IoT devices 151-152 of the third party establishments 141-142 may be used for assisting in the gathering of ingestion information for users who visit the respective establishments, e.g., a restaurant, a cafeteria and the like. In one example, the servers 161-162 of the third party establishments 141-142 are used for storing and/or exchanging nutritional information to and from the application server 104 by the establishments 141-142, respectively.

In one example, the third party establishment 141 may comprise a restaurant or a school (broadly an educational institution), e.g., a chain of fast food restaurants, or a university. The IoT device 151 or 152 may comprise a sensor for determining a food or drink item that is consumed by a user visiting the restaurant or school. In another example, the third party establishment 142 may comprise a store that sells items (food and/or drink) to be ingested. For instance, the third party establishment 142 may be a grocery store. In one embodiment, the IoT devices 151-152 may also determine the identity of the user consuming the food or drink item, e.g., via a scanner or an RF reader by detecting a fingerprint, an RF tag code, a cell phone number and the like. The identity of the user can then be provided to server 161 or 162. Using the detected identity, ingestion information pertaining to the ingestion of various detected food and drink items can be transmitted by server 161 or 162 to AS 104 on behalf of the user. In other words, in one example food and drink items consumed outside of a user's home can also be related to AS 104 on behalf of the user. For example, a smart dish of a restaurant is utilized for serving a particular type of food to a patron, e.g., an egg omelet having certain additional ingredients such as spinach, mushroom and onion. Since the restaurant is the preparer of this particular food item, the restaurant is in the best position to convey what the food item is actually formulated from. In turn, the ingredients (broadly ingestion information) used to make an entree can be accurately communicated directly to AS 104 or to a mobile endpoint device of the user.

In another embodiment, the identity of the user does not need to be identified by the server 161 or 162. For example, if user 110 is visiting the establishment 141 and is served via the IoT device 151 (e.g., a smart dish or container), the UE 117 of user 110 may receive an input from the IoT device 151 indicative of the user 110 being served via the IoT device 151. Similarly, if user 110 is visiting the establishment 142 and is served via the IoT device 152 (e.g., a smart dish or container), the UE 117 of user 110 may receive an input from the IoT device 152 indicative of the user 110 being served via the IoT device 152. Thus, the ingestion information associated with the food and drink items consumed in these third party establishments can be directly communicated to the UE 117. In one embodiment, the IoT device may communicate with UE 117 via a Wi-Fi network, Bluetooth interface, etc. to provide to the UE 117 information regarding food and/or drink items that are ingested by the user 110.

In one example, the establishments 141-142 may subscribe to a service to receive nutritional information that has been aggregated over a geographical area from a network service provider. For example, such "aggregated" nutritional information has been anonymized such that personal information has been removed. Said another way, the nutritional information of a group of individuals are aggregated to provide information as to what food/drink items are being consumed by a local population, but the personal information relating to the group of individuals are removed and not disclosed to any third party establishments to maintain the privacy of the group of individuals. For example, a restaurant or grocery store may wish to know the nutritional needs of a local population served by the restaurant or grocery store. For instance, for a local population during the winter season, fruit juice consumption may be detected to be increasing due to a large segment of the local population wishing to increase vitamin C intake during the winter months. In turn, the grocery store and restaurant may benefit by stocking such appropriate products. Thus, the establishments 141-142 may receive aggregated nutritional information that is aggregated for a population for a local geographical area, e.g., within a one mile radius, within a two mile radius, within a town, and so on. The application server 104 may then send the nutritional information that is aggregated to servers 161-162 of the third party establishments. In one embodiment, the nutritional information may be stored in a cloud storage and the establishments may be enabled to access the information. For example, the third party establishments may access an aggregated nutritional information from a database 105 of the service provider.

Figure 2:
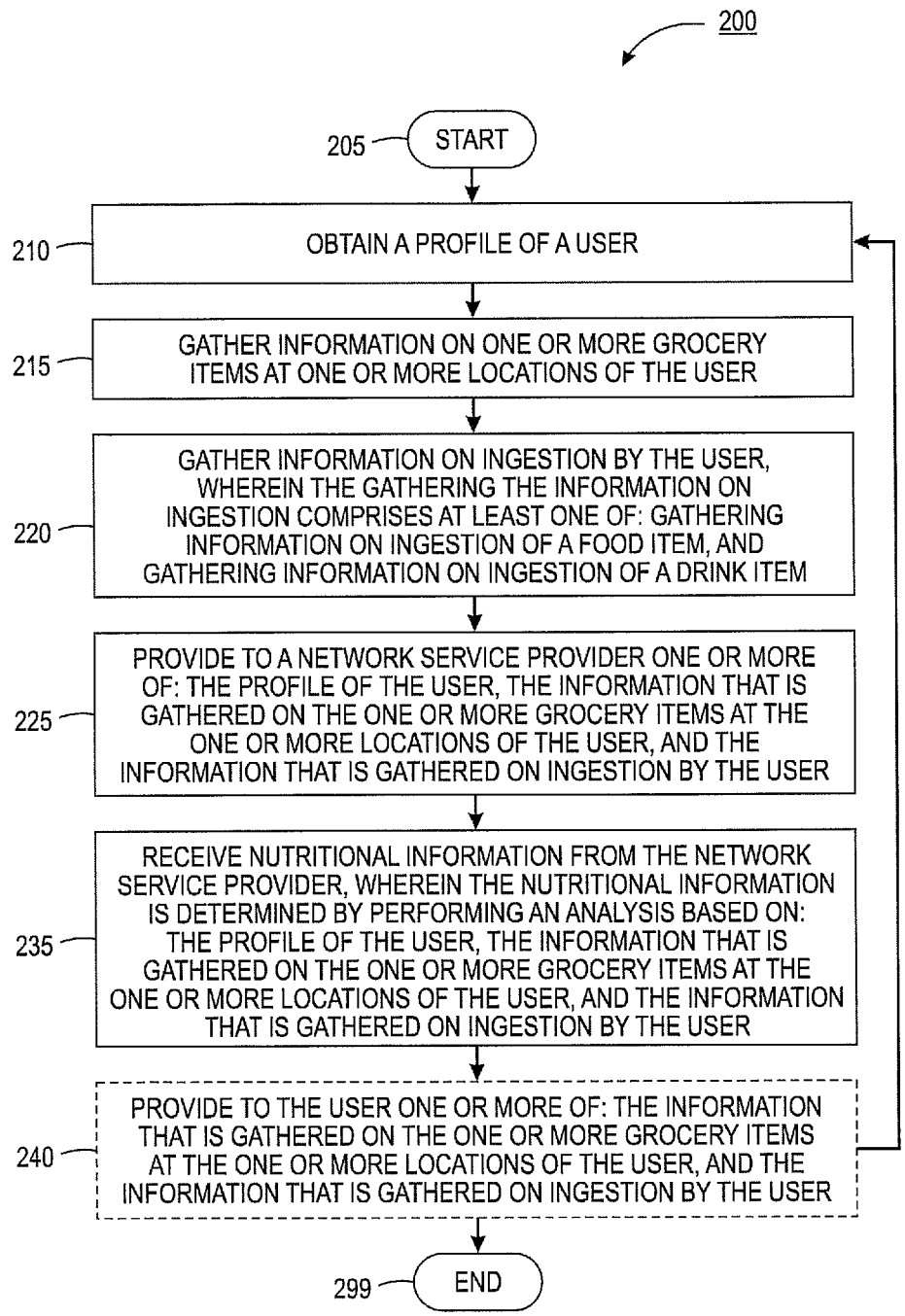
FIG. 2 illustrates a flowchart of an example method for receiving nutritional information.

FIG. 2 illustrates a flowchart of an example method 200 for receiving nutritional information in accordance with the present disclosure. In one embodiment, the method 200 may be implemented in an endpoint device of a user, e.g., an UE 117, or the processor 402 as described in FIG. 4. The method 200 starts in step 205 and proceeds to step 210.

In step 210, the processor obtains a profile of a user. In one embodiment, various information pertaining to the profile of the user can be automatically obtained via one or more IoT devices, e.g., in-home IoT devices of the user. In another embodiment, various information pertaining to the profile of the user can be obtained via a user interface for receiving the profile from the user. For example, the user may provide to the UE, via the user interface, the user's age, the user's gender, the user's race, etc. In another example, the user's weight may be received from an IoT device that comprises a scale, the user's blood pressure may be determined via an IoT device that comprises a sphygmomanometer, the user's glucose level may be determines via an IoT device that comprises a glucometer, the user's heart rate may be determined via an IoT device that comprises a heart rate monitor, and so on.

In one embodiment, each IoT device transmits the relevant profile information of the user to the endpoint device of the user, and then the endpoint device of the user may aggregate the profile information collected from a plurality of the IoT devices into a consolidated profile to be transmitted to the service provider. In another embodiment, each IoT device may transmit the relevant profile information of the user directly to a server of the service provider. In another embodiment, the IoT device may transmit the relevant profile information of the user to a cloud storage device. Similarly, the endpoint device may upload the consolidated profile to the server of the network service provider or store the consolidated profile at a cloud storage accessible by the server of the network service provider. It should be noted that the collection and transmission of the profile information are performed with the authority and full consent of the user, e.g., the user has consented and has subscribed to a nutritional information service provided by the network service provider.

In step 215, the processor gathers information on one or more available grocery items at one or more locations of the user. In one embodiment, the gathering of the information on a grocery item of the one or more grocery items may be performed via an IoT device in which the grocery item is stored.

For example, the IoT device in which the grocery item is stored transmits the information on the grocery item to the user endpoint device. For instance, if the IoT device is at a residence of the user, the IoT device may be a smart refrigerator and/or freezer, a smart pantry, a smart cabinet, a smart disposer, and the like. The IoT device in the residence may then transmit to the user endpoint device, information on grocery items that are stored in the IoT device. The user endpoint device may then provide the information to the network service provider.

In one embodiment, the IoT device may also transmit the information on the available grocery item directly to a server of the service provider. For example, the IoT device may be at a location (e.g., a university cafeteria) shared with other individuals. The IoT device may then identify the user via a biometric scanner or via a communication with the UE of the user, e.g., via a Bluetooth connection between the IoT device and the cell phone of the user. The IoT device may then transmit to the service provider information gathered on available grocery items for the user. For example, if the user is a student of a university and frequents a particular cafeteria on campus, the available grocery items offered by this particular cafeteria can be provided to the network service provider. Again, the fact that the grocery items are available does not mean that the user has actually ingested any of the available grocery items.

In one embodiment, the IoT device and the user endpoint device may transmit the information on the grocery item to a cloud storage device. In other words, the sensors 132-134 and the user endpoint device 117 may upload the information on the grocery item to a server of the network service provider or store the information on the grocery item at a cloud storage accessible by the server of the network service provider.

In step 220, the processor gathers ingestion information on ingestion of food and/or drink items (e.g., at least one grocery item from the grocery information of step 215) by the user, wherein the gathering the ingestion information on ingestion comprises at least one of: gathering information on ingestion of a food item and gathering information on ingestion of a drink item. In one embodiment, the gathering the ingestion information on the ingestion of the food item is performed via a vessel or dish for containing the food item. In one embodiment, the gathering the ingestion information on the ingestion of the drink item is performed via a vessel or container for containing the drink item. In one embodiment, the ingestion information that is gathered on ingestion by the user comprises one or more of: when the food item is consumed, a type of the food item (e.g., fruit, vegetable, meat, bread, dessert, etc.) that is consumed, a quantity of the food item that is consumed, and an identity of the user consuming the food item. In one embodiment, the information that is gathered on ingestion by the user comprises one or more of: when the drink item is consumed, a type of the drink item (e.g., juice, milk, alcoholic beverage, water, etc.) that is consumed, a quantity of the drink item that is consumed, and an identity of the user consuming the drink item.

In one embodiment, the vessel for containing the food or the drink item may comprise an IoT device. For example, the vessel may be a smart dish 125 or a smart container 126. The vessel for containing the food item (e.g., smart dish 125) may comprise a sensor for determining one or more of: when the food item is consumed, a type of the food item (e.g., fruit, vegetable, meat, bread, dessert, etc.) that is consumed, a quantity of the food item that is consumed, and so on. Similarly, the vessel for containing the drink item (e.g., smart container 126) may comprise a sensor for determining one or more of: when the drink item is consumed, a type of the drink item (e.g., water, juice, etc.) that is consumed, and a quantity of the drink item that is consumed.

In one embodiment, the vessel for containing the food item or drink item may further comprise a sensor for determining an identity of the user consuming the food item or drink item. For example, the sensor for determining the identity of the user consuming the food item or the drink item may comprise a biometric scanner. For example, the smart dish or smart container may include a biometric scanner that comprises a fingerprint scanner, a retina scanner, a voiceprint scanner, and the like.

In one embodiment, the vessel for containing the food item may send a record of the food item being consumed to the user endpoint device, an application server, and/or a cloud storage. In one embodiment, the vessel for containing the drink item may also send a record of the drink item being consumed to the user endpoint device, the application server, and/or the cloud storage.

In step 225, the processor provides to a network service provider one or more of: the profile of the user, the information that is gathered on the one or more grocery items at the one or more locations of the user, and the ingestion information that is gathered on the ingestion of at least one item from the one or more grocery items by the user. For example, if user 110 removes a can of soup from a smart pantry 123, places the soup on a smart dish 125, eats half of the soup and then discards the remaining residual in a disposer 124, the UE 117 receives from the smart pantry 123 (which includes sensor 133) information on the fact that user 110 has removed one can of soup, e.g., including the type of soup and the size of the can. The UE 117 receives from the smart dish 125 that the entire content of the can of soup has been placed onto the dish and the residual amount that is left over and not consumed (e.g., an amount of content that remains on the dish for an extended period of time and then followed by a rapid emptying of the dish, e.g., the content being dumped into a disposer 124). In addition, if the smart dish 125 has a scanner, the smart dish 125 also identifies that user 110 is the person using the smart dish 125 to consume the soup. The UE 117 also receives from the disposer 124 that a dumped content consistent with soup has been disposed by user 110. For example, the dumped content can be identified by a captured image or from information received from a smart dish being proximate to the disposer when the dumped content was received (e.g., presumably the dumped content came from the smart dish). The UE 117 is then able to gather such ingestion information to determine the amount of soup that is consumed and the amount of soup that is discarded, the time of consumption (e.g., via time stamps collected by each IoT or sensor), the time of disposal (e.g., via time stamps collected by each IoT or sensor), which member of the household consumed the soup, and so on. The UE 117 then provides to the AS 104 of the network service provider the profile of the user, the information gathered to determine the amount of soup that is consumed, the amount of soup discarded, the time of consumption, the time of disposal, which member of the household consumed the soup, and so on.

In one embodiment, the information gathered on the grocery items and ingestion information may be provided to the network service provider frequently, while the profile is updated and/or provided to the network service provider with less frequency. The profile of the user may not change frequently. For instance, the information gathered on grocery items and ingestion information may be provided to the network service provider, e.g., on a weekly basis, on a daily basis, on an hourly basis, at every occurrence of ingestion, at every occurrence of storage, removal or disposing of a grocery item. The profile of the user may be provided in accordance with a longer interval, e.g., weekly, monthly, quarterly, etc.

In step 235, the processor receives nutritional information from the network service provider, wherein the nutritional information is determined by performing an analysis based on: the profile of the user, the information that is gathered on the one or more grocery items at the one or more locations of the user, and the ingestion information that is gathered on ingestion by the user. In one embodiment, the analysis is further based on nutritional information of a population at the one or more locations of the user. For example, the network service provider may identify a segment of the population at the one or more locations of the user with profiles that match the user. For instance, the segment of the population may be population with a same gender, similar height, similar weight, similar race, and so on. The network service provider may then analyze the ingestion information for a particular segment of the population. For example, the data gathered for the particular segment of the population may provide a distribution for various nutritional indicators. For instance, the nutritional indicators may be for ingestions of one or more of: each type of vitamin, each type of mineral, water, protein, fiber, fat, various types of fat (e.g., unsaturated, saturated, animal based, plant based), vitamin/mineral supplements, sugar, types of sugar, and the like. The data may then be analyzed to establish a baseline for the particular segment of the population for each nutritional indicator. For example, the baseline may provide a mean, median, standard deviation, etc., of the various nutritional indicators for the particular segment of the population. The user's ingestion of food and drink items over a predetermined duration of time may then be compared to the baseline for the particular segment of the population. For example, compared to people matching the profile of the user, the user may be drinking an insufficient amount of water, e.g., 32 ounces below the mean water intake for a segment of the population matching his/her profile. In turn, the UE of the user may receive nutritional information from the network service provider that indicates that the user needs to drink 32 ounces more of water per day to reach the mean consumption of water, e.g., 50 ounces to be in the top quartile, etc.

In optional step 240, the processor provides to the user one or more of: the information that is gathered on the one or more grocery items at the one or more locations of the user, and the ingestion information that is gathered on ingestion by the user. For example, the UE 117 may provide the gathered information to the user. In one embodiment, the gathered information is presented to the user via a display of the UE. The method then either returns to step 210, or to step 299 to end the process.

Figure 3:
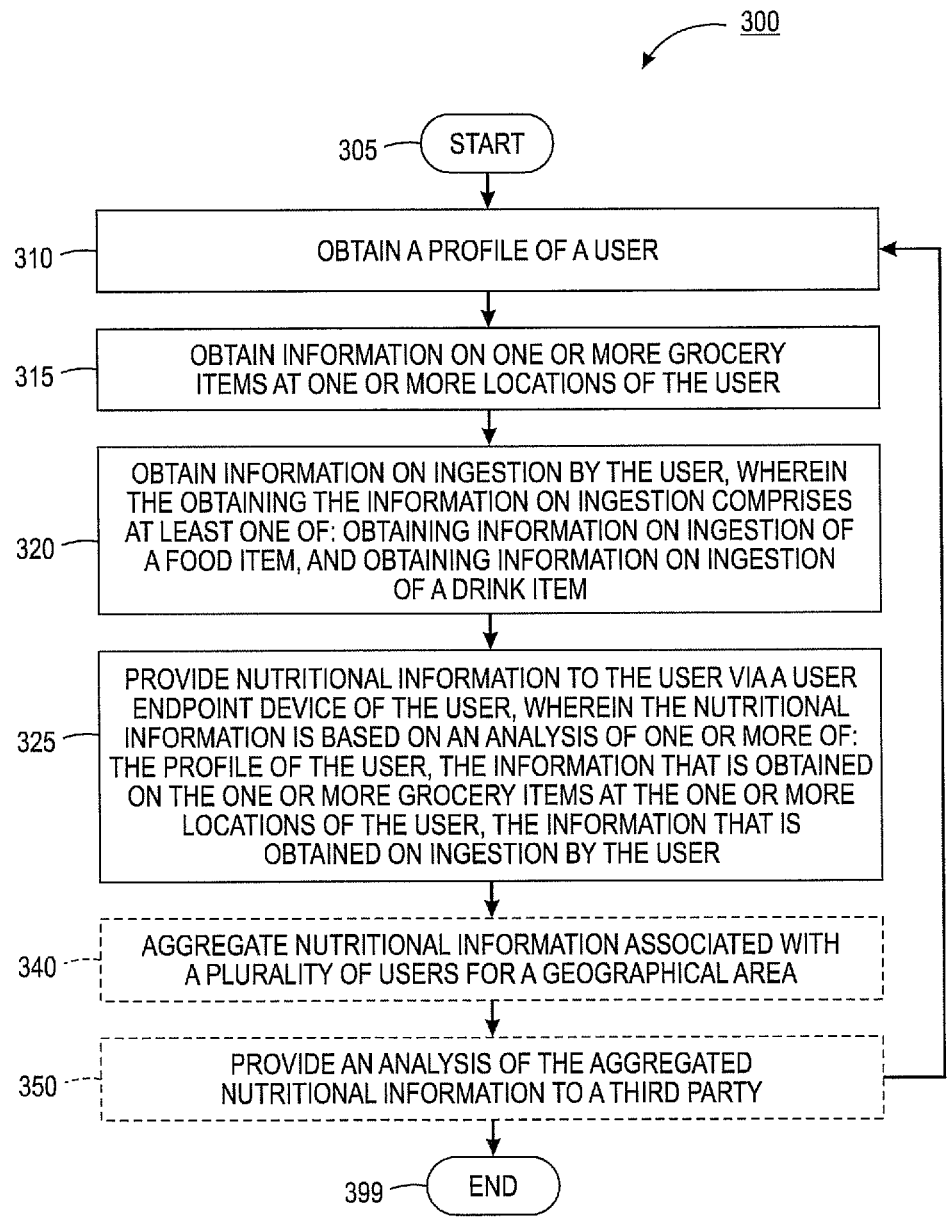
FIG. 3 illustrates a flowchart of an example method for providing nutritional information.

FIG. 3 illustrates a flowchart of an example method 300 for providing nutritional information in accordance with the present disclosure. In one embodiment, the method 300 may be implemented in an application server of a network service provider, e.g., AS 104, or the processor 402 as described in FIG. 4. The method 300 starts in step 305 and proceeds to step 310.

In step 310, the processor obtains or receives a profile of a user. In one embodiment, the profile of the user is obtained or received from a user endpoint device of the user. In one embodiment, information pertaining to the profile of the user can also be obtained or received via one or more IoT devices. In one embodiment, the profile of the user may be obtained such that some portion of the profile is received from the user endpoint device and the remaining portion of the profile is received via one or more IoT devices. For example, the UE may provide the age, gender, race, etc., of the user. In another example, IoT devices may provide the user's weight, blood pressure, glucose level, heart rate, body temperature, etc.

In step 315, the processor obtains or receives information on one or more grocery items at one or more locations of the user. In one embodiment, the obtaining or receiving of the information on a grocery item of the one or more grocery items is performed via a user endpoint device associated with the user. For example, the information may be obtained or received via the cell phone of the user. In one embodiment, the obtaining of the information on a grocery item of the one or more grocery items is performed via a gateway server of the user. In one embodiment, the obtaining or receiving of the information on a grocery item of the one or more grocery items is performed via an IoT device in which a grocery item is stored.

In step 320, the processor obtains or receives ingestion information on ingestion of food and/or drink items (e.g., at least one grocery item from the received grocery information of step 315) by the user, wherein the obtaining or receiving the ingestion information on ingestion comprises at least one of: obtaining information on ingestion of a food item and obtaining information on ingestion of a drink item. In one embodiment, the obtaining of the ingestion information on ingestion is performed via a user endpoint device associated with the user. In one embodiment, the obtaining of the ingestion information on ingestion is performed via a gateway server of the user. In one embodiment, the obtaining or receiving of the ingestion information on ingestion of food and/or drink items by the user is performed via an IoT device.

In one embodiment, the IoT device used for obtaining of the information on ingestion comprises a vessel for containing the food item. In one embodiment, the vessel for containing the food item comprises a sensor for determining one or more of: when the food item is consumed, a type of the food item (e.g., fruit, vegetable, meat, bread, dessert, etc.) that is consumed, and a quantity of the food item that is consumed. In one embodiment, the vessel for containing the food item further comprises a sensor for determining an identity of the user consuming the food item. In one embodiment, the sensor for determining the identity of the user consuming the food item may comprise a biometric scanner. In one embodiment, the biometric scanner may comprise one or more of: a fingerprint scanner, a retina scanner, and a voiceprint scanner.

In one embodiment, the IoT device used for obtaining of the information on ingestion comprises a vessel for containing the drink item. In one embodiment, the vessel for containing the drink item comprises a sensor for determining one or more of: when the drink item is consumed, a type of the drink item (e.g., water, juice, etc.) that is consumed, and a quantity of the drink item that is consumed. In one embodiment, the vessel for containing the drink item further comprises a sensor for determining an identity of the user consuming the drink item. In one embodiment, the sensor for determining the identity of the user consuming the drink item may comprise a biometric scanner. In one embodiment, the biometric scanner may comprise one or more of: a fingerprint scanner, a retina scanner, and a voiceprint scanner.

In one example, if the IoT device is at a residence of the user, the IoT device may be a smart refrigerator and/or freezer, a smart pantry, a smart dish, a smart container, and the like. The IoT devices in the residence may transmit to the UE device. The UE device may then transmit to the server provider information gathered via any number of IoT devices. In another example, the user may implement a centralized gateway (e.g., a dedicated computer) for gathering information from various IoT devices and for providing combined information to an application server of the network service provider. For instance, a home gateway computer may gather information on: profile of the user (e.g., via scales, heart rate monitor, etc.), grocery items (e.g., refrigerator, pantry, etc.) and ingestion of food and drink items (e.g., via smart dishes and containers). In yet another example, the IoT devices may directly transmit to the application server of the service provider.

In step 325, the processor provides nutritional information to the user via a user endpoint device of the user, wherein the nutritional information is based on an analysis of one or more of: the profile of the user, the information that is obtained on the one or more grocery items at the one or more locations of the user, the ingestion information that is obtained on ingestion of food and/or drink items by the user. In one embodiment, the analysis is further based on a comparison of the ingestion by the user with a baseline for ingestions computed for a population or against a model selected by the user. For example, the network service provider may analyze the ingestion information for a particular segment of the population with a profile comparable to that of the user. The analysis may be used to establish a baseline for the particular segment of the population. For example, the baseline may provide a mean, median, standard deviation, etc., of the various nutritional indicators for the particular segment of the population whose profile is comparable to that of the user. The user's ingestion of food and drink items over a predetermined duration of time may then be compared to the baseline that is established for the particular segment of the population. In turn, the network service provider may then provide to the user the nutritional information based on the comparison.

In optional step 340, the processor aggregates nutritional information associated with a plurality of users for a geographical area. For example, the nutritional information of the plurality of users, e.g., for a city, a town, a zip code, a defined area such as a one mile radius, may be aggregated. For instance, the aggregated nutritional information may indicate for each food or drink item of the one or more food or drink items: a quantity of the food or drink item being consumed by users in the geographical area, a population profile of the users consuming the food or drink item, etc. For an illustrative example, women within the geographical area are drinking four cups of water and one cup of milk, men are drinking six cups of water, children are drinking two cups of water and two cups of milk, etc. However, no personal information will be provided in the aggregated nutritional information. Namely, the privacy of the users will be maintained unless specifically authorized by the users to be disclosed.

In optional step 350, the processor provides an analysis of the aggregated nutritional information to a third party. For example, the method may analyze the aggregated nutritional information associated with the plurality of users for the geographical area. The result of the analysis may then be provided to a third party.

In one embodiment, the third party may comprise an establishment that provides the grocery items to users in the geographical area. For example, the establishment may be a grocery store, a store that delivers grocery items via a mail service, and the like.

In one embodiment, the third party may comprise an establishment that provides a food item or a drink item that is prepared. For example, the establishment may be a diner, restaurant, bar, juice bar, coffee shop, a school that provides meals to students, and the like. The method then either returns to step 310, or to step 399 to end the process.

In addition, although not specifically specified, one or more steps, functions or operations of method 200 or method 300 may include a storing, displaying and/or outputting step as required for a particular application. In other words, any data, records, fields, and/or intermediate results discussed in the method can be stored, displayed and/or outputted either on the device executing the method or to another device, as required for a particular application.

Furthermore, steps, blocks, functions or operations in FIG. 2 or FIG. 3 that recite a determining operation or involve a decision do not necessarily require that both branches of the determining operation be practiced. In other words, one of the branches of the determining operation can be deemed as an optional step. Moreover, steps, blocks, functions or operations of the above described method 200 or 300 can be combined, separated, and/or performed in a different order from that described above, without departing from the example embodiments of the present disclosure.

It should be noted that the above described method can be deployed with various different implementations. For example, the receiving the nutritional information may be via a dedicated computer. In one embodiment, the IoT devices may directly provide the information gathered on grocery items and ingestion by the user to the service provider. Hence, the UE device of the user may be for receiving the nutritional information after the IoT devices provided the data directly to the service provider. In one embodiment, the dedicated computer is for gathering information on grocery items, gathering information on ingestion, interacting with the user to receive the profile of the user, receiving further profiles via IoT devices, providing the information to the network service provider for analysis and comparison with data from a large population or model selected by the user, and for receiving the nutritional information from the network service provider.

In one example, the present method for receiving nutritional information of the present disclosure is implemented via a dedicated database server. For example, in one embodiment, the method of the present disclosure is implemented via a dedicated application server, e.g., AS 104, for providing the nutritional information to user endpoint device, e.g., to UE 117. The dedicated application server is operated and managed by a network service provider. For example, the network service provider may operate one or more communications networks to provide one or more services such as telephony services, cellular services, data services (e.g., data access and transfer services, Internet access services, and the like), multimedia delivery services (e.g., multimedia programming delivery services such as movies, videos, music and the like), and the like. In another embodiment, the present method for receiving nutritional information can be provided in the user endpoint device, e.g., UE 117.

As such, the present disclosure provides at least one advancement in the technical field of receiving nutritional information based on a baseline of nutritional need of an individual (established based on a profile of the individual) and a record of ingestion by the individual. This advancement improves the ability of the user to utilize his/her nutritional information for health improvement. For example, the user is then able to take an appropriate action that is reflective of the baseline of the nutritional behavior of the general population or a model. The present disclosure also provides at least one advancement in the technical field of providing nutritional information of individuals to a network service provider. The network service provider is then able to aggregate the data, perform analytics on nutritional intake of populations in a geographical area, provide feedback to individuals on nutritional intake based on the analytics, and/or provide to a third party (e.g., a grocery store, restaurant, a school, etc.) nutritional intake information based on the analytics.

FIG. 4 depicts a high-level block diagram of a computer suitable for use in performing the functions described herein. As depicted in FIG. 4, the system 400 comprises one or more hardware processor elements 402 (e.g., a central processing unit (CPU), a microprocessor, or a multi-core processor), a memory 404, e.g., random access memory (RAM) and/or read only memory (ROM), a module 405 for receiving nutritional information, and various input/output devices 406 (e.g., storage devices, including but not limited to, a tape drive, a floppy drive, a hard disk drive or a compact disk drive, a receiver, a transmitter, a speaker, a display, a speech synthesizer, an output port, an input port and a user input device (such as a keyboard, a keypad, a mouse, a microphone and the like)). Although only one processor element is shown, it should be noted that the computer may employ a plurality of processor elements. Furthermore, although only one computer is shown in the figure, if the method 200 or method 300 as discussed above is implemented in a distributed or parallel manner for a particular illustrative example, i.e., the steps of the above method 200 or method 300, or each of the entire method 200 or method 300 is implemented across multiple or parallel computers, then the computer of this figure is intended to represent each of those multiple computers.

Furthermore, one or more hardware processors can be utilized in supporting a virtualized or shared computing environment. The virtualized computing environment may support one or more virtual machines representing computers, servers, or other computing devices. In such virtualized virtual machines, hardware components such as hardware processors and computer-readable storage devices may be virtualized or logically represented.

It should be noted that the present disclosure can be implemented in software and/or in a combination of software and hardware, e.g., using application specific integrated circuits (ASIC), a programmable gate array (PGA) including a Field PGA, or a state machine deployed on a hardware device, a computer or any other hardware equivalents, e.g., computer readable instructions pertaining to the method(s) discussed above can be used to configure a hardware processor to perform the steps, functions and/or operations of the above disclosed method.

In one embodiment, instructions and data for the present module or process 405 for receiving nutritional information (e.g., a software program comprising computer-executable instructions) can be loaded into memory 404 and executed by hardware processor element 402 to implement the steps, functions or operations as discussed above in connection with the illustrative method 200 or method 300. Furthermore, when a hardware processor executes instructions to perform "operations," this could include the hardware processor performing the operations directly and/or facilitating, directing, or cooperating with another hardware device or component (e.g., a co-processor and the like) to perform the operations.

The processor executing the computer readable or software instructions relating to the above described method can be perceived as a programmed processor or a specialized processor. As such, the present module 405 for receiving nutritional information (including associated data structures)

of the present disclosure can be stored on a tangible or physical (broadly non-transitory) computer-readable storage device or medium, e.g., volatile memory, non-volatile memory, ROM memory, RAM memory, magnetic or optical drive, device or diskette and the like. Furthermore, a "tangible" computer-readable storage device or medium comprises a physical device, a hardware device, or a device that is discernible by the touch. More specifically, the computer-readable storage device may comprise any physical devices that provide the ability to store information such as data and/or instructions to be accessed by a processor or a computing device such as a computer or an application server.

While various embodiments have been described above, it should be understood that they have been presented by way of example only, and not a limitation. Thus, the breadth and scope of a preferred embodiment should not be limited by any of the above-described exemplary embodiments, but should be defined only in accordance with the following claims and their equivalents.

What is claimed is:

1. A method comprising:
receiving, via a processor of a network service provider, a profile of a user;
receiving, via the processor and over a packet network associated with the network service provider, from at least a first internet of things device, grocery information on an availability of one or more grocery items for ingesting by the user at one or more locations of the user, wherein the grocery information includes an image of a machine-readable code affixed to the one or more grocery items, and wherein the at least the first internet of things device comprises at least one selected from a group of: a refrigerator, a freezer, or a cabinet;
identifying, via the processor, a type of the one or more grocery items based on the machine-readable code;
receiving, via the processor and over the packet network associated with the network service provider, from at least a second internet of things device, ingestion information on ingestion by the user of at least one grocery item of the one or more grocery items, wherein the at least the second internet of things device is distinct from the at least the first internet of things device, and wherein the at least the second internet of things device comprises at least one selected from a group of: a vessel for containing the at least one grocery item, a food serving dish for containing the at least one grocery item, a plate for containing the at least one grocery item, a bowl for containing the at least one grocery item, a drinking container for containing the at least one grocery item, a cup for containing the at least one grocery item, a glass for containing the at least one grocery item, a mug for containing the at least one grocery item, or a tumbler for containing the at least one grocery item;
generating, via the processor, nutritional information, wherein the nutritional information is determined by performing an analysis based on the profile of the user, the grocery information, the type of the one or more grocery items, and the ingestion information, and wherein the nutritional information is further based on aggregated nutritional information of a population at the one or more locations of the user, and wherein the nutritional information further indicates a recommended adjustment to the ingestion by the user of the at least one grocery item based on the aggregated nutritional information; and
providing, via the processor and over the packet network associated with the network service provider, the nutritional information including the recommended adjustment, to an endpoint device of the user.

2. The method of claim 1, wherein the profile of the user is received via one or more of the at least the first internet of things device.

3. The method of claim 1, wherein the profile of the user is received via the endpoint device of the user.

4. The method of claim 1, wherein the at least the first internet of things device comprises at least one internet of things device in which at least one grocery item from the one or more grocery items is stored.

5. The method of claim 1, wherein the grocery information is further received from an internet of things device comprising a disposer.

6. The method of claim 1, wherein the at least the second internet of things device comprises an internet of things device with a sensor for determining one or more of: when the at least one grocery item is consumed, a type of the at least one grocery item that is consumed, and a quantity of the at least one grocery item that is consumed.

7. The method of claim 6, wherein the at least the second internet of things device further comprises a sensor for determining an identity of the user consuming the at least one grocery item.

8. The method of claim 7, wherein the sensor for determining the identity of the user consuming the at least one grocery item comprises a biometric scanner.

9. The method of claim 8, wherein the biometric scanner comprises at least one of: a fingerprint scanner, a retina scanner, or a voiceprint scanner.

10. The method of claim 6, wherein the at least one grocery item comprises a food item.

11. The method of claim 6, wherein the at least one grocery item comprises a drink item.

12. The method of claim 1, wherein the nutritional information is further based on a nutritional model selected by the user.

13. The method of claim 1, wherein the at least one grocery item comprises a food item and a drink item, wherein the ingestion information comprises one or more of: a time when the food item is consumed, a type of the food item that is consumed, a quantity of the food item that is consumed, an identity of the user consuming the food item, a time when the drink item is consumed, a type of the drink item that is consumed, a quantity of the drink item that is consumed, and an identity of the user consuming the drink item.

14. The method of claim 1, further comprising:
providing, via the processor, the nutritional information to an application server of a third party establishment.

15. The method of claim 14, wherein the third party establishment comprises a grocery store, a restaurant, or an educational institution.

16. The method of claim 1, wherein the at least the first internet of things device is connected to the packet network via a first wireless communication protocol, and wherein the at least the second internet of things device is connected to the packet network via a second wireless protocol different from the first wireless communication protocol.

17. A non-transitory computer-readable storage device storing a plurality of instructions which, when executed by a processor of a packet network operated by a network service provider, cause the processor to perform operations, the operations comprising:

receiving a profile of a user;

receiving over the packet network from at least a first internet of things device, grocery information on an availability of one or more grocery items for ingesting by the user at one or more locations of the user, wherein the grocery information includes an image of a machine-readable code affixed to the one or more grocery items, and wherein the at least the first internet of things device comprises at least one selected from a group of: a refrigerator, a freezer, or a cabinet;

identifying a type of the one or more grocery items based on the machine-readable code;

receiving over the packet network from at least a second internet of things device, ingestion information on ingestion by the user of at least one grocery item of the one or more grocery items, wherein the at least the second internet of things device is distinct from the at least the first internet of things device, and wherein the at least the second internet of things device comprises at least one selected from a group of: a vessel for containing the at least one grocery item, a food serving dish for containing the at least one grocery item, a plate for containing the at least one grocery item, a bowl for containing the at least one grocery item, a drinking container for containing the at least one grocery item, a cup for containing the at least one grocery item, a glass for containing the at least one grocery item, a mug for containing the at least one grocery item, or a tumbler for containing the at least one grocery item;

generating nutritional information, wherein the nutritional information is determined by performing an analysis based on the profile of the user, the grocery information, the type of the one or more grocery items, and the ingestion information, and wherein the nutritional information is further based on aggregated nutritional information of a population at the one or more locations of the user, and wherein the nutritional information further indicates a recommended adjustment to the ingestion by the user of the at least one grocery item based on the aggregated nutritional information; and providing over the packet network, the nutritional information including the recommended adjustment, to an endpoint device of the user.

18. An apparatus comprising:

a processor of a packet network operated by a network service provider; and a computer-readable storage device storing a plurality of instructions which, when executed by the processor, cause the processor to perform operations, the operations comprising:

receiving a profile of a user;

receiving over the packet network from at least a first internet of things device, grocery information on an availability of one or more grocery items for ingesting by the user at one or more locations of the user, wherein the grocery information includes an image of a machine-readable code affixed to the one or more grocery items, and wherein the at least the first internet of things device comprises at least one selected from a group of: a refrigerator, a freezer, or a cabinet;

identifying a type of the one or more grocery items based on the machine-readable code;

receiving over the packet network from at least a second internet of things device, ingestion information on ingestion by the user of at least one grocery item of the one or more grocery items, wherein the at least the second internet of things device is distinct from the at least the first internet of things device, and wherein the at least the second internet of things device comprises at least one selected from a group of: a vessel for containing the at least one grocery item, a food serving dish for containing the at least one grocery item, a plate for containing the at least one grocery item, a bowl for containing the at least one grocery item, a drinking container for containing the at least one grocery item, a cup for containing the at least one grocery item, a glass for containing the at least one grocery item, a mug for containing the at least one grocery item, or a tumbler for containing the at least one grocery item;

generating nutritional information, wherein the nutritional information is determined by performing an analysis based on the profile of the user, the grocery information, the type of the one or more grocery items, and the ingestion information, and wherein the nutritional information is further based on aggregated nutritional information of a population at the one or more locations of the user, and wherein the nutritional information further indicates a recommended adjustment to the ingestion by the user of the at least one grocery item based on the aggregated nutritional information; and providing over the packet network, the nutritional information including the recommended adjustment, to an endpoint device of the user.

19. The apparatus of claim 18, wherein the at least the second internet of things device comprises an internet of things device with a sensor for determining one or more of: when the at least one grocery item is consumed, a type of the at least one grocery item that is consumed, and a quantity of the at least one grocery item that is consumed.

20. The apparatus of claim 19, wherein the at least the second internet of things device further comprises a sensor for determining an identity of the user consuming the at least one grocery item.

* * * * *